(12) United States Patent
Pang et al.

(10) Patent No.: US 11,053,539 B2
(45) Date of Patent: Jul. 6, 2021

(54) DETECTION SUBSTRATE AND MANUFACTURING METHOD THEREOF, AND NUCLEIC ACID DETECTING METHOD

(71) Applicants: BOE Technology Group Co., Ltd., Beijing (CN); Beijing BOE Optoelectronics Technology Co., Ltd., Beijing (CN)

(72) Inventors: Fengchun Pang, Beijing (CN); Peizhi Cai, Beijing (CN); Yue Geng, Beijing (CN)

(73) Assignees: BOE Technology Group Co., Ltd., Beijing (CN); Beijing BOE Optoelectronics Technology Co., Ltd., Beijing (CN)

( * ) Notice: Subject to any disclaimer, the term of this patent is extended or adjusted under 35 U.S.C. 154(b) by 420 days.

(21) Appl. No.: 15/750,907

(22) PCT Filed: Jul. 12, 2017

(86) PCT No.: PCT/CN2017/092594
§ 371 (c)(1),
(2) Date: Feb. 7, 2018

(87) PCT Pub. No.: WO2018/099088
PCT Pub. Date: Jun. 7, 2018

(65) Prior Publication Data
US 2020/0087721 A1 Mar. 19, 2020

(30) Foreign Application Priority Data
Dec. 1, 2016 (CN) .......................... 201611091734.0

(51) Int. Cl.
*B01L 3/00* (2006.01)
*C12Q 1/6869* (2018.01)
*C12Q 1/6825* (2018.01)

(52) U.S. Cl.
CPC ......... *C12Q 1/6869* (2013.01); *C12Q 1/6825* (2013.01); *C12Q 2525/191* (2013.01);
(Continued)

(58) Field of Classification Search
CPC ........................................................ B01L 3/00
See application file for complete search history.

(56) References Cited

U.S. PATENT DOCUMENTS 6,071,395 A 6/2000 Lange
7,462,452 B2 * 12/2008 Williams ............. C12Q 1/6869
435/6.11
(Continued)

FOREIGN PATENT DOCUMENTS

CN 102639716 A 8/2012
CN 103354838 A 10/2013
(Continued)

OTHER PUBLICATIONS

Merriam-Webster, definition of "hollow," available at https://www.merriam-webster.com/dictionary/hollow, accessed May 20, 2020.*
(Continued)

*Primary Examiner* — Aaron A Priest
(74) *Attorney, Agent, or Firm* — Banner & Witcoff, Ltd.

(57) ABSTRACT

A detection substrate and a manufacturing method thereof, and a nucleic acid detecting method are provided. The detection substrate includes at least one detection unit disposed on a base substrate, the detection unit including a first electrode, a second electrode and a colloid layer, the second electrode disposed on a side of the first electrode away from the base substrate, the second electrode including at least one hollowed structure, the second electrode and the first electrode being insulated from each other, and the first electrode and the second electrode being configured to be applied with voltages respectively; the colloid layer at least
(Continued)

disposed on the at least one hollowed structure of the second electrode, the colloid layer including a linker configured to be paired with a target nucleic acid.

18 Claims, 6 Drawing Sheets

(52) U.S. Cl.
CPC .. *C12Q 2531/113* (2013.01); *C12Q 2535/122* (2013.01); *C12Q 2563/107* (2013.01); *C12Q 2565/607* (2013.01)

(56) References Cited

U.S. PATENT DOCUMENTS

| | | | |
|---|---|---|---|
| 8,888,969 B2* | 11/2014 | Soleymani | G01N 27/30 204/289 |
| 9,500,617 B2 | 11/2016 | Credo et al. | |
| 2002/0090649 A1 | 7/2002 | Chan et al. | |
| 2004/0248282 A1 | 12/2004 | Sobha M. et al. | |
| 2005/0084865 A1* | 4/2005 | Yu | C12Q 1/6834 435/6.11 |
| 2005/0274612 A1 | 12/2005 | Segawa et al. | |
| 2006/0228740 A1* | 10/2006 | Seul | C12Q 2565/501 435/6.11 |
| 2009/0081371 A1 | 3/2009 | Minami et al. | |
| 2011/0294691 A1* | 12/2011 | Erickson | G01N 21/658 506/9 |
| 2012/0122715 A1 | 5/2012 | Gao et al. | |
| 2013/0345085 A1 | 12/2013 | Togawa | |
| 2015/0047976 A1* | 2/2015 | Setford | C12Q 1/006 204/403.01 |
| 2016/0249840 A1* | 9/2016 | Pesantez | C12Q 1/005 205/778 |
| 2017/0010238 A1* | 1/2017 | Johnson | C12Q 1/001 |
| 2017/0283796 A1 | 10/2017 | Shirai et al. | |
| 2019/0025249 A1* | 1/2019 | Koh | G01N 27/4145 |
| 2019/0136307 A1* | 5/2019 | Predki | G01N 33/48721 |
| 2020/0102613 A1* | 4/2020 | Turner | C12Q 1/6874 |

FOREIGN PATENT DOCUMENTS

| | | |
|---|---|---|
| JP | 2009092651 A | 4/2009 |
| JP | 2007040832 A1 | 2/2015 |

OTHER PUBLICATIONS

Merriam-Webster, definition of "away," available at https://www.merriam-webster.com/dictionary/away, accessed May 20, 2020.*
Merriam-Webster, definition of "sub," available at https://www.merriam-webster.com/dictionary/sub, accessed Oct. 27, 2020.*
Sep. 20, 2017—(WO) International Search Report and Written Opinion Appn PCT/CN2017/092594 with English Translation.
Dec. 9, 2020—(EP) Extended European Search Report Appn 17835577.2.
Sep. 27, 2020—(CN) First Office Action Appn 201611091734.0 with English Translation.
Apr. 19, 2021—(JP) First Office Action Appn 2018-506273 with English Translation.

* cited by examiner

# DETECTION SUBSTRATE AND MANUFACTURING METHOD THEREOF, AND NUCLEIC ACID DETECTING METHOD

The application is a U.S. National Phase Entry of International Application No. PCT/CN2017/092594 filed on Jul. 12, 2017, designating the United States of America and claiming priority to Chinese Patent Application No. 201611091734.0, filed Dec. 1, 2016. The present application claims priority to and the benefit of the above-identified applications and the above-identified applications are incorporated by reference herein in their entirety.

TECHNICAL FIELD

At least one embodiment of the present disclosure relates to a detection substrate and a manufacturing method thereof, and a nucleic acid detecting method.

BACKGROUND

The gene sequencing technology is a most commonly used technology in modern molecular biology study. From a first generation of gene sequencing in 1977 to now, the gene sequencing technology has been greatly developed. The gene sequencing technology includes the first generation of sanger sequencing technology, the second generation of high throughput sequencing technology, the third generation of single molecule sequencing technology and the fourth generation of nano-pore sequencing technology. The mainstream of current market is still centered on the second generation of high throughput sequencing technology.

The second generation of the high throughput sequencing technology mainly includes Illumina's sequencing-by-synthesis technology, Thermo Fisher's ion semiconductor sequencing technology, sequencing-by-ligation technology, and Roche's pyrosequencing technology etc. The Illumina holds more than 70% of market share by virtue of advantages of super high throughput and relative long read length.

The illumina's sequencing technology cuts a target DAN into small fragments, and then different linkers are added to two ends of the fragment, to construct a single-stranded DNA library. A bridge polymerase chain reaction (PCR) is performed on a flow cell by using the single-stranded DNA library as a template, to generate a lot of DNA clusters, and each of the DNA clusters includes a lot of copies of a single target DNA; finally, DNA polymerases, primers, and fluorescently labeled bases are added to the flow cell, and when the bases are bound to the DNA, fluorescent signals are excited by laser and are captured by a corresponding optical device, and finally, the optical signals are transformed to a base sequence by computer analysis.

SUMMARY

At least one embodiment of the disclosure provides a detection substrate and a manufacturing method thereof, and a nucleic acid detecting method, which performs the amplification and detection of the nucleic acid by applying voltages to the first electrode and the second electrode of the detection unit respectively. A requirement on the structure and appearance of the first electrode and the second electrode is simple, which simplifies the process difficulty.

At least one embodiment of the disclosure provides a detection substrate comprising at least one detection unit disposed on a base substrate, the detection unit comprising:
a first electrode;
a second electrode, disposed on a side of the first electrode away from the base substrate, the second electrode comprising at least one hollowed structure, the second electrode and the first electrode being insulated from each other, and the first electrode and the second electrode being configured to be applied with voltages respectively;
a colloid layer, at least disposed on the at least one hollowed structure of the second electrode, the colloid layer comprising a linker configured to be paired with a target nucleic acid.

According to the detection substrate provided by one embodiment of the disclosure, the first electrode and the second electrode of at least one detection unit are configured to be applied with voltages with different polarities respectively.

According to the detection substrate provided by one embodiment of the disclosure, in a direction perpendicular to the base substrate, the first electrode is at least overlapped with the at least one hollowed structure.

According to the detection substrate provided by one embodiment of the disclosure, the first electrode is a plane-shaped electrode.

According to the detection substrate provided by one embodiment of the disclosure, the second electrode comprises at least one sub-electrode unit, and one hollowed structure is enclosed by one sub-electrode unit.

According to the detection substrate provided by one embodiment of the disclosure, the second electrode comprises a plurality of sub-electrode units, and the plurality of the sub-electrode units are electrically connected.

According to the detection substrate provided by one embodiment of the disclosure, further comprises a first passivation layer disposed between the first electrode and the second electrode and a second passivation layer disposed between the second electrode and the colloid layer.

According to the detection substrate provided by one embodiment of the disclosure, further comprises a coupling layer disposed between the second passivation layer and the colloid layer.

According to the detection substrate provided by one embodiment of the disclosure, a material of the coupling layer comprises silane.

According to the detection substrate provided by one embodiment of the disclosure, the detection substrate comprises a plurality of detection units.

According to the detection substrate provided by one embodiment of the disclosure, the plurality of the detection units are arranged in an array.

According to the detection substrate provided by one embodiment of the disclosure, the colloid layer comprises a gel layer.

At least one embodiment of the disclosure provides a manufacturing method of a detection substrate, comprising forming at least one detection unit on a base substrate, forming the detection unit comprising:
forming a first electrode,
forming a second electrode, the second electrode being disposed on a side of the first electrode away from the base substrate, the second electrode comprising at least one hollowed structure, the second electrode and the first electrode being insulated from each other and configured to be applied with voltages respectively;
forming a colloid layer, the colloid layer comprising a linker configured to be paired with a target nucleic acid.

According to the manufacturing method of the detection substrate provided by one embodiment of the disclosure, the first electrode and the second electrode of at least one detection unit are configured to be applied with voltages with different polarities respectively.

According to the manufacturing method of the detection substrate provided by one embodiment of the disclosure, in a direction perpendicular to the base substrate, the first electrode is at least overlapped with the at least one hollowed structure.

According to the manufacturing method of the detection substrate provided by one embodiment of the disclosure, further comprises forming a first passivation layer between the first electrode and the second electrode and forming a second passivation layer between the second electrode and the colloid layer.

According to the manufacturing method of the detection substrate provided by one embodiment of the disclosure, further comprises forming a coupling layer between the second passivation layer and the colloid layer.

According to the manufacturing method of the detection substrate provided by one embodiment of the disclosure, the colloid layer comprises a gel layer.

At least one embodiment of the disclosure further provides a nucleic acid detecting method, comprising:

taking the at least one detection unit of the detection substrate of any one of the embodiments of the present disclosure as an active unit, applying voltages with different polarities to the first electrode and the second electrode of the active unit respectively, the voltage applied to the first electrode of the active unit having a polarity opposite to a polarity of an electric charge of the target nucleic acid;

flowing a library through the detection substrate, the linker in the active unit being paired with the target nucleic acid of the library, and performing an amplification to form a target nucleic acid to be detected;

detecting the target nucleic acid to be detected.

According to the nucleic acid detecting method provided by one embodiment of the disclosure, the detection substrate comprises a plurality of detection units, the first electrode and the second electrode of each of the detection units other than the active unit are applied with voltages with a same polarity, the polarity of the voltages applied to the first electrode and the second electrode of each of the detection units other than the active unit is the same as the polarity of the electric charge of the target nucleic acid.

According to the nucleic acid detecting method provided by one embodiment of the disclosure, the detection substrate comprises a plurality of detection units, different detection units are taken as the active unit sequentially, and the first electrode and the second electrode of each of the detection units other than the active unit are applied with voltages having the same polarity as that of the electric charge of the target nucleic acid, different libraries are flowed through the detection substrate to perform the amplification and the detection in different active units.

According to the nucleic acid detecting method provided by one embodiment of the disclosure, detecting the target nucleic acid to be detected comprising:

contacting the detection substrate with at least one fluorescently labeled probe configured to be bound to the target nucleic acid to be detected;

detecting a fluorescent signal on the detection substrate to recognize the target nucleic acid to be detected bound with the at least one probe.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for invention, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

In the Illumina's sequencing technology, a flow cell is a key component of the gene sequencing. In order to improve the sequencing throughput, the flow cell is patterned, and a lot of nano-wells are etched on a flow channel. Because nano-wells are not overlapped with each other, there is no interference between fluorescent signals, which can improve the utilization of the flow cell, and improve the sequencing throughput. Because the PCR amplification and the gene sequencing are performed in the nano-wells, the requirement on a structure of the nano-well is very strict, resulting in a complicated manufacturing process.

Figure 1A:
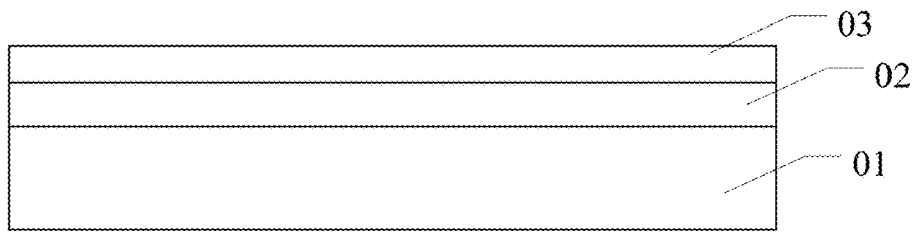
FIGS. 1a-1h are a nano-well and a manufacturing method thereof.
Figure 1B:
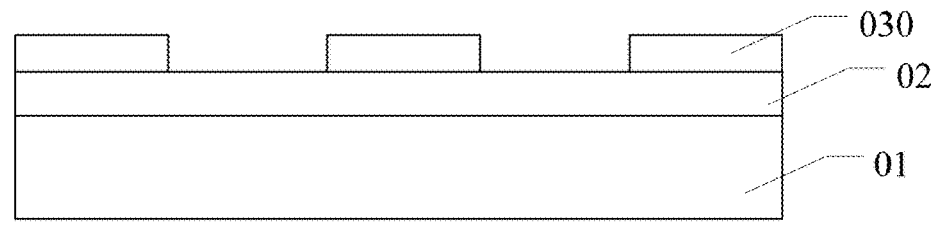
Figure 1C:
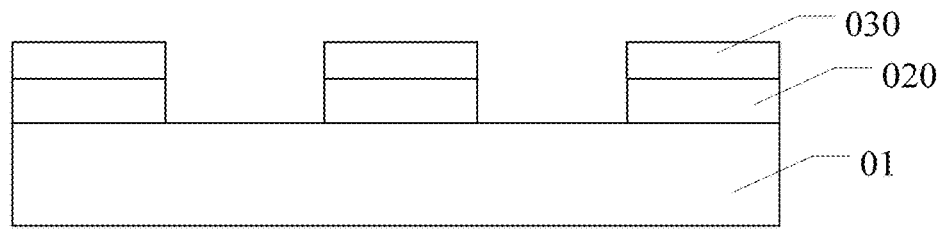
Figure 1D:
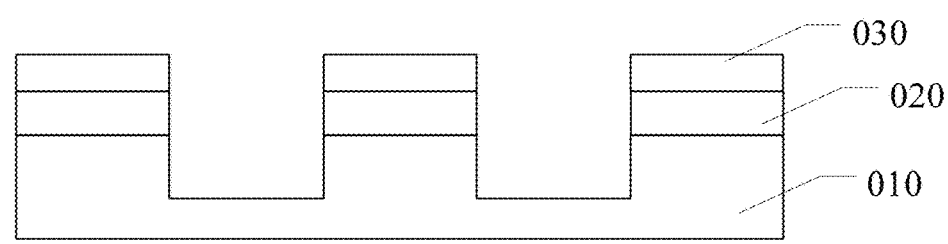
Figure 1E:
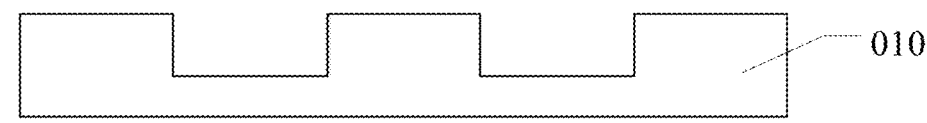
Figure 1F:
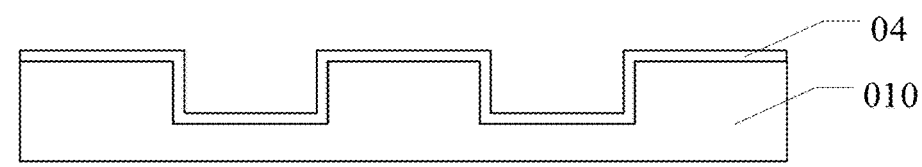
Figure 1G:
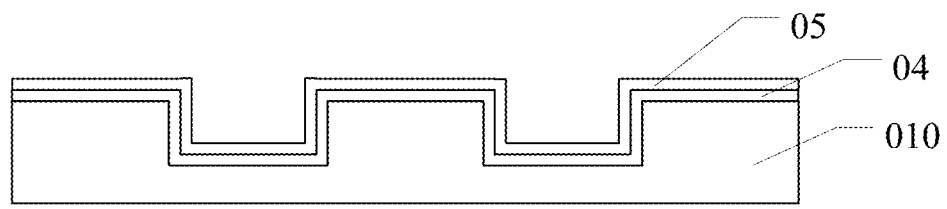
Figure 1H:
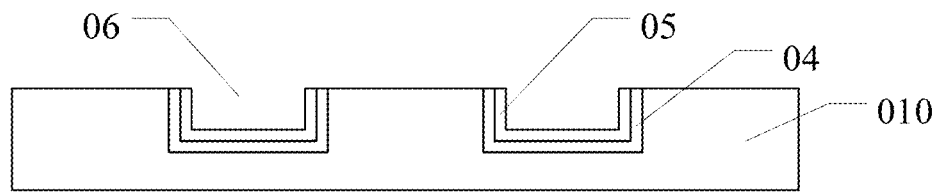

FIGS. 1a-1h illustrate the Illumina's manufacturing process of a nano-well. As illustrated in FIG. 1a, a metal layer 102 is sputtered on a base substrate 01, the metal layer is a sacrifice layer, and a material of the metal layer can be Cr, for example. Then a photoresist layer 03 is spin coated, and by using the lithography, the photoresist layer is exposed and developed to remove the exposed photoresist so as to form a patterned photoresist 030, as illustrated in FIG. 1b. As illustrated in FIG. 1c, the metal which is not protected by the photoresist is etched by using the patterned photoresist 030 as a mask, and then, as illustrated in FIG. 1d, a portion of the base substrate which is not protected by the photoresist is etched. As illustrated in FIG. 1e, the remained photoresist and the remained metal are stripped off, to obtain a patterned base substrate 010. As illustrated in FIG. 1f, a silane layer 04 is spin coated on the patterned base substrate 010, to perform a surface processing. As illustrated in FIG. 1g, a gel layer 05 is spin coated, a DNA linker is contained in the gel and can be paired with the template DNA, and finally, a mechanical or chemical polishing is performed, to remove the silane and gel in gaps between the nano-wells, so as to ensure that the gel configured to be paired with a DNA is only disposed in the nano-wells 06, to obtain the nano-well structure as illustrated in FIG. 1h. For example, the base substrate can be Si or glass etc., and the nano-imprinting technology can also be adopted to manufacture nano-wells. Such a method has strict requirements on nano-well properties, and at the same time, has a strict requirement on uniformity of the nano-wells, and thus it is difficult to etch the base substrate.

At least one embodiment of the disclosure provides a detection substrate, including at least one detection unit disposed on a base substrate, the detection unit includes:

a first electrode, a second electrode, disposed on a side of the first electrode away from the base substrate, the second electrode including at least one hollowed structure, the second electrode and the first electrode being insulated from each other, and the first electrode and the second electrode being configured to be applied with voltages respectively;

a colloid layer, at least disposed on the at least one hollowed structure of the second electrode, the colloid layer including a linker configured to be paired with a target nucleic acid.

The detection substrate provided by at least one embodiment of the disclosure utilizes the first electrode and the second electrode of the detection unit to be applied with voltages respectively to perform the amplification (for example, the PCR amplification) and the detection (for example, the sequencing) of a target nucleic acid. For example, the first electrode is applied with a voltage having a polarity opposite to a polarity of an electric charge of the target nucleic acid, and the second electrode is applied with a voltage having the same polarity as that of a polarity of the electric charge of the target nucleic acid, so that a structure similar to the nano-well can be formed. The target nucleic acid can be paired with a linker in the detection unit, so that the amplification and detection of the target nucleic acid can be performed. A requirement on the structure and appearance of the first electrode and the second electrode is simple, thereby reducing the process difficulty.

At least one embodiment of the disclosure further provides a manufacturing method of a detection substrate, including forming at least one detection unit on a base substrate, forming the detection unit includes:

forming a first electrode, forming a second electrode, the second electrode disposed on a side of the first electrode away from the base substrate, the second electrode including at least one hollowed structure, the second electrode and the first electrode being insulated from each other, and the first electrode and the second electrode being configured to be applied with voltages respectively;

forming a colloid layer, the colloid layer including a linker configured to be paired with a target nucleic acid.

The manufacturing method of the detection substrate provided by at least one embodiment of the disclosure has a simple requirement on the structure and the appearance of the first electrode and the second electrode, has a simple manufacturing process and does not need to perform a surface polishing process.

At least one embodiment of the disclosure further provides a nucleic acid detecting method, including:

taking at least one detection unit of any one of the detection substrates provided by the at least one embodiment of the disclosure as an active unit, applying different voltages to the first electrode and the second electrode of the active unit respectively, the voltage applied to the first electrode of the active unit having a polarity opposite to a polarity of an electric charge of the target nucleic acid;

flowing a library through the detection substrate, the linker in the active unit being paired with the target nucleic acid of the library, and performing an amplification to form a target nucleic acid to be detected; and detecting the target nucleic acid to be detected.

The nucleic acid detecting method provided by the at least one embodiment of the disclosure can control the power-on condition of the first electrode and the second electrode in different regions so as to control different libraries to be loaded to different regions without using a barcode to distinguish libraries, and more libraries can be sequenced in one time, a precision control is achieved. Thus, a flow of the nucleic acid detection is simplified, a detection time is shortened and a detection cost is reduced.

The following is a description of several embodiments.

First Embodiment

Figure 2A:
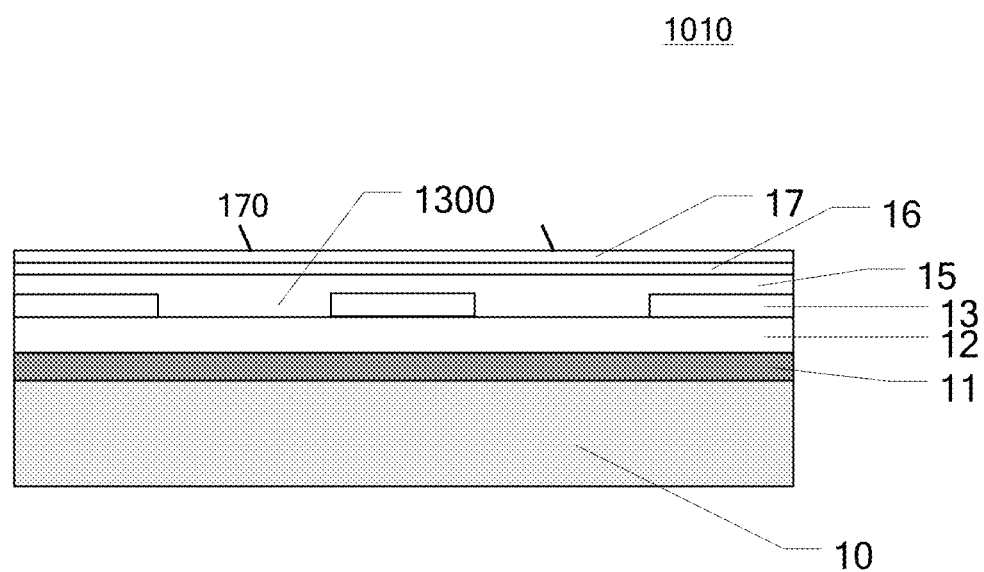
FIG. 2a is a schematic cross-sectional diagram of a detection substrate provided by an embodiment of the disclosure.

The embodiment provides a detection substrate 1010, as illustrated in FIG. 2a, including at least one detection unit 100 disposed on a base substrate 10.

Figure 2B:
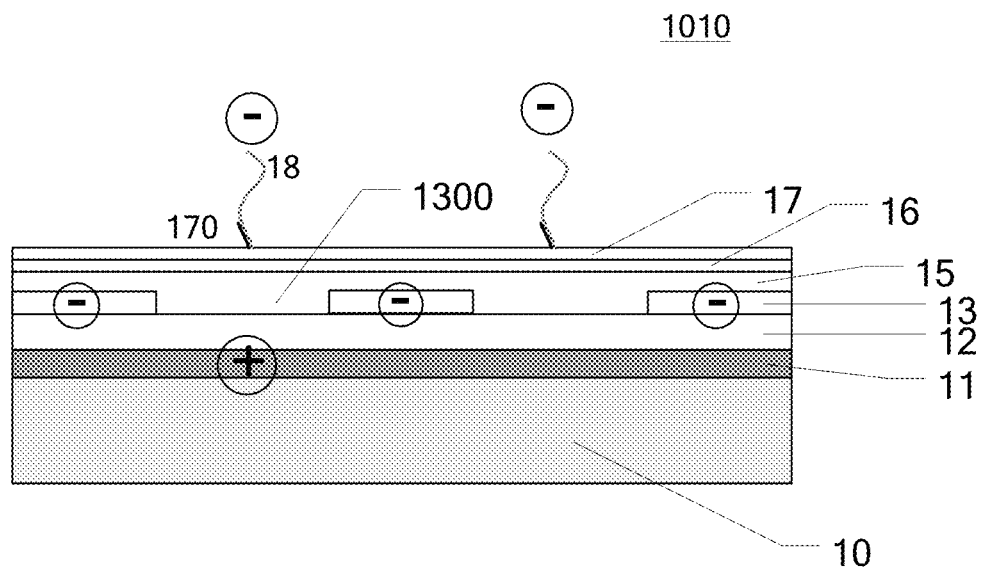
FIG. 2b is a schematic diagram of a nucleic acid being paired with a linker of a detection substrate provided by an embodiment of the disclosure.

The detection unit 100 includes:

a first electrode 11, a second electrode 13, disposed on a side of the first electrode 11 away from the base substrate 10, the second electrode 13 including at least one hollowed structure 1300, the second electrode 13 and the first electrode 11 being insulated from each other, and the first electrode 11 and the second electrode 13 being configured to be applied with voltages respectively;

a colloid layer 17, at least disposed on at least one hollowed structure 1300 of the second electrode 13, the colloid layer 17 including a linker 170 configured to be paired with a target nucleic acid 18 (not illustrated in FIG. 2a, please refer to FIG. 2b). For example, as illustrated in FIG. 2b, the linker 170 is paired with a portion of the target nucleic acid 18 to facilitate a following amplification of the target nucleic acid. The colloid layer 17 is configured to accommodate the linker 170.

For example, a voltage having a polarity opposite to the polarity of the electric charge of the target nucleic acid 18 can be applied to the first electrode 11, to attract the target nucleic acid to be paired with the linker. For example, the polarity of the electric charge of the target nucleic acid 18 can be determined by an experiment or an environment where it is located, but it is not limited to this. For example, the polarity of the electric charge of the target nucleic acid is related to the environment where it is located. For example, the target nucleic acid can be with a negative electric charge in an alkaline environment. For example, the target nucleic acid 18 can be with a negative electric charge in an alkaline solution due to presence of the phosphate residues. For example, in the embodiment, the polarity includes a positive polarity and a negative polarity. For example, having a same polarity refers to both of the polarities are positive or negative. Having opposite polarities refers to one of them is positive and the other is negative.

The detection substrate provided by the embodiment can utilize the first electrode and the second electrode of the detection unit to be applied with voltages respectively to perform the amplification (for example, the PCR amplification) and the detection (for example, the sequencing) of the target nucleic acid. A requirement on the structure and appearance of the first electrode and the second electrode is simple, which simplifies the process difficulty.

For example, the target nucleic acid 18 can be bound to the linker 170 of the gel material by base pairing, and the linker 170 can be configured to amplify the target nucleic acid bound therewith. That is, the target nucleic acid can be used as a template for amplification. For example, the linker 170 can be paired with a linker of the target nucleic acid 18. The linker 170 can be a primer, for example, it can be a primer nucleic acid, but it is not limited to this. For example, the target nucleic acid can also be referred as a template nucleic acid. The linker 170 can adopts a conventional linker, and can be attached into the colloid layer 17 by a conventional method. For example, a plurality of linkers 170 can be included in each of the detection units 100, and thus a clonal population of the target nucleic acid can be formed. For example, each of the detection units 100 includes two kinds of linkers 170 to perform a bridge PCR amplification. For example, the target nucleic acid 18 can be a single-stranded deoxyribonucleic acid (DNA) fragment, but it is not limited to this.

The colloid layer 17 can adopt a conventional material, and for example, the colloid layer 17 can be a gel layer. For example, the gel layer can include a hydrogel. For further example, a colloidal structure material, a polymer mesh structure material, or a cross-linked polymer structure material can be adopted. For example, the colloidal structure material includes agarose. For example, the polymer mesh structure material includes gelatin. For example, the cross-linked polymer structure material includes polyacrylamide. The material of the colloid layer can also be silane-free acrylamide or N-[5-(2-bromoacetyl) amidogen amyl] acrylic amide (BRAPA). It should be noted that, the material of the colloid layer 17 is not limited to above listed cases.

For example, the first electrode 11 and the second electrode 13 of the at least one detection unit 100 is configured to be applied with voltages with different polarities. The at least one detection unit in which the first electrode 11 and the second electrode 13 are applied with voltages with different polarities can be referred as an active unit. For example, as illustrated in FIG. 2b, the first electrode 11 is applied with a voltage having a polarity opposite to a polarity of the electric charge of the target nucleic acid 18, and thus, the target nucleic acid can be attracted to the first electrode 11 at a position corresponding to the hollowed structure 1300 of the second electrode 13, so that the target nucleic acid 18 can be paired with the linker 170. The second electrode 13 is applied with a voltage having the same polarity as that of the electric charge of the target nucleic acid; therefore, even though a linker 170 exists at a position corresponding to the second electrode 13, the target nucleic acid 18 would not be paired with the linker 170 due to the repulsive effect, and thus, a structure similar to the nano-well can be formed, so that the target nucleic acid 18 can be paired with the linker 170 within the active unit in the detection substrate, and the amplification and detection of the target nucleic acid can be performed. For example, different target nucleic acids can be bound to different detection units 100, but it is not limited to this.

Figure 3A:
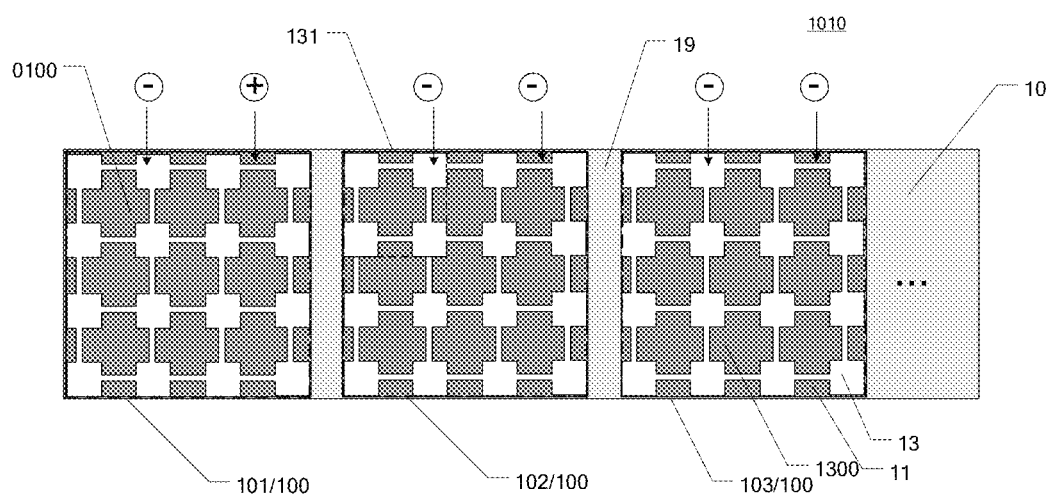
FIG. 3a is a schematic top view of another detection substrate provided by an embodiment of the disclosure.
Figure 3B:
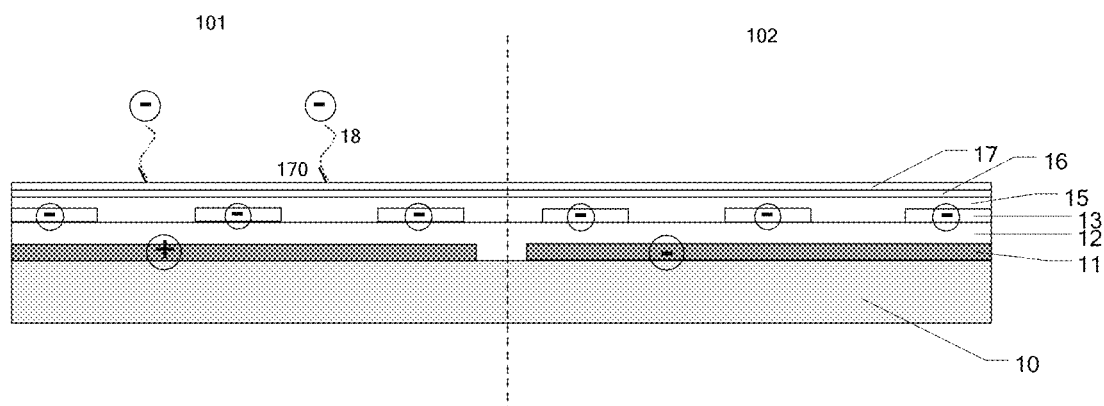
FIG. 3b is a schematic diagram of power-on condition of different detection units of a detection substrate provided by an embodiment of the disclosure.

For example, as illustrated in FIGS. 2a, 2b and 3a, in a direction perpendicular to the base substrate 10, the first electrode 11 is at least overlapped with at least one hollowed structure 1300. Thus, in a region corresponding to the hollowed structure, the voltage applied to the first electrode 11 can attract the target nucleic acid having an electric charge of opposite polarity thereto to the detection unit 100, so that the linker 170 within the detection unit 100 is paired with the target nucleic acid. As illustrated in FIGS. 2b and 3b, the target nucleic acid 18 with a negative electric charge is taken as an example to illustrate. If the target nucleic acid 18 is negatively charged, a positive voltage can be applied to the first electrode 11 and a negative voltage can be applied to the second electrode 13. It should be noted that, the embodiment is not limited to this.

For example, as illustrated in FIG. 3a, the first electrode 11 can be a plane-shaped electrode. The plane-shaped electrode is easily formed and easily manufactured. But the first electrode 11 is not limited to the plane-shaped electrode. For example, the first electrode 11 can also only correspond to the hollowed structure 1300 of the second electrode 13. For example, the first electrode 11 at least includes a portion corresponding to the hollowed structure 1300 of the second electrode 13. That is, in a direction perpendicular to the base substrate 10, the first electrode is at least overlapped with the at least one hollowed structure 1300 formed in (included in) the second electrode 13.

For example, as illustrated in FIG. 3a, the second electrode 13 can include at least one sub-electrode unit 131, and one hollowed structure 1300 is enclosed by one sub-electrode unit 131. For example, as illustrated in FIG. 3a, the second electrode 13 can include a plurality of sub-electrode units 131, and the plurality of the sub-electrode units 131 are electrically connected. Different sub-electrode units 131 can have a shared portion. The second electrode 13 illustrated in FIG. 3a can have different widths at different positions, but it is not limited to this. For example, the second electrode 13 can also have a same width at different positions.

For example, as illustrated in FIGS. 2b and 3b, the detection substrate 1010 further includes a first passivation layer 12 disposed between the first electrode 11 and the second electrode 13 and a second passivation layer 15 disposed between the second electrode 13 and the colloid layer 17. The first passivation layer 12 and the second passivation layer 15 can be planarization layers, but it is not limited to this. The first passivation layer 12 is provided so that the first electrode 11 and the second electrode 13 can be insulated from each other. The second passivation layer 15 is provided so that the colloid layer can be easily formed. For example, the first passivation layer 12 and the second passivation layer 15 can adopt a conventional material. For example, the first passivation layer 12 and the second passivation layer 15 can adopt tantalum oxide, but it is not limited to this. For example, the first passivation layer 12 and the second passivation layer 15 can also adopt SiOx, SiNx, SiNxOy or resin etc.

For example, as illustrated in FIGS. 2a and 3b, the detection substrate can further include a coupling layer 16 disposed between the second passivation layer 15 and the colloid layer 17. The coupling layer 16 is employed to make the colloid layer 17 attach to the base substrate 10 more firmly. For example, a material of the coupling layer 16 includes silane, but it is not limited to this.

For example, as illustrated in FIG. 3a, the detection substrate can include a plurality of the detection units 100. The detection units are not overlapped with each other, so that there is no interference between fluorescent signals in detection, which can improve the utilization of the detection substrate, improve the sequencing throughput and achieve high throughput sequencing. FIG. 3a only illustrates three detection units 100, i.e. the first detection unit 101, the second detection unit 102 and the third detection unit 130, and the number of the detection units is not limited to those as illustrated in the figures.

At different times, the amplification and detection can be performed in different detection units according to power-on condition of the detection units. For example, as illustrated in FIG. 3b, at a certain time, in the detection unit (active unit 0100, the first detection unit 101 as illustrated in FIGS. 3a and 3b) in which the first electrode 11 and the second electrode 13 are applied with voltages having opposite polarities, the amplification and the detection are performed. However, in the detection unit (inactive unit, the second detection unit 102 and the third detection unit 103) in which the first electrode 11 and the second electrode 13 are applied with voltages having the same polarity as that of the polarity of the electric charge of the target nucleic acid, the target nucleic acid is not paired with the linker, and no amplification occurs. At different times, the power-on condition of the first electrode and the second electrode of different detection units (regions) can be controlled, so as to control different libraries to be loaded in different regions without using a barcode to distinguish libraries, and more libraries can be sequenced at one time, thereby achieving a precision control. Thus, a flow of the nucleic acid detection is simplified, a detection time is shortened and a detection cost is reduced.

Figure 3C:
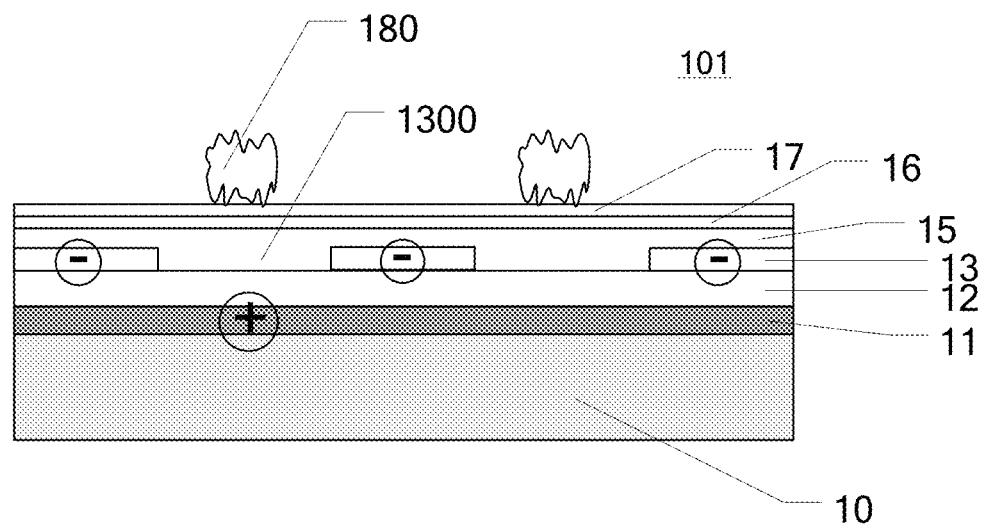
FIG. 3c is a schematic diagram of a target nucleic acid being amplified to a cluster in an active unit of a detection substrate provided by an embodiment of the disclosure
Figure 3D:
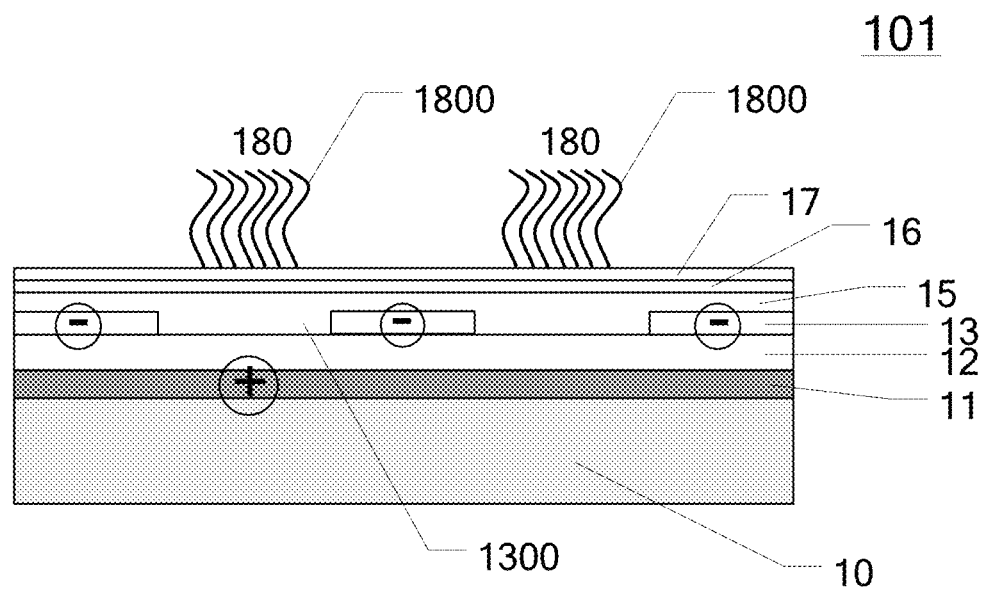
FIG. 3d is a schematic diagram of a target nucleic acid cluster to be detected of a detection substrate provided by an embodiment of the disclosure.

As illustrated in FIG. 3c, after the amplification, a target nucleic acid cluster to be detected 180 can be formed. As illustrated in FIG. 3d, the target nucleic acid cluster to be detected 180 includes a plurality of target nucleic acids to be detected 1800, to facilitate enhancement of the fluorescent signals during a following detecting process. It should be noted that, the number of the target nucleic acids to be detected 1800 included in the target nucleic acid cluster to be detected 180 is not limited to those as illustrated in the figures, and the appearance of the target nucleic acid to be detected 1800 is not limited to those as illustrated in figures. For example, the target nucleic acid to be detected 1800 and the target nucleic acid 18 can have complementary sequences, but it is not limited to this. For example, the target nucleic acid to be detected 1800 and the target nucleic acid 18 can also have the same sequence.

For example, a plurality of the detection units can be arranged in an array, but it is not limited to this. For example, they can also be arranged in other forms. For example, the plurality of the detection units can be distributed randomly. For example, the linkers 170 in the colloid layers 17 of different detection units 100 can be same, and can also be different, which can be determined according to requirements, and will not be limited by the embodiment. For example, as illustrated in FIG. 3a, the colloid layer 17 shown in FIG. 3b) may not be provided on a region (gap region 19) between different detection units 100, or the gap region 19 of the colloid layer 17 can be made inactive, so that outward migration of the growing nucleic acid cluster is prevented. The amplification of the target nucleic acid 18 is limited within the detection unit 100, and the amplification of the target nucleic acid is only performed in the region corresponding to the hollowed region 1300.

For example, the first electrode 11 and the second electrode 13 of each of the detection units 100 can be connected with respective wires to facilitate to be applied with signals.

Second Embodiment

The embodiment provides a manufacturing method of a detection substrate 1010, including forming at least one detection unit 100 on a base substrate 10.

Forming the detection unit 100 includes:
forming a first electrode 11,
forming a second electrode 13, the second electrode 13 disposed on a side of the first electrode 11 away from the base substrate 10, the second electrode 13 including at least one hollowed structure 1300, the second electrode 13 and the first electrode 11 being insulated from each other, and the first electrode 11 and the second electrode 13 being configured to be applied with voltages respectively;
forming a colloid layer 17, the colloid layer 17 including a linker 170 configured to be paired with a target nucleic acid 18.

For example, the first electrode 11 and the second electrode 13 of the at least one detection unit 100 are configured to be applied with voltages with different polarities respectively.

For example, in a direction perpendicular to the base substrate 10, the first electrode 11 is at least overlapped with at least one hollowed structure 1300.

For example, the manufacturing method of the detection substrate 1010 further includes forming a first passivation layer 12 between the first electrode 11 and the second electrode 13 and forming a second passivation layer 15 between the second electrode 13 and the colloid layer 17.

For example, the manufacturing method of the detection substrate 1010 further includes forming a coupling layer 16 between the second passivation layer 15 and the colloid layer 17.

In one example, the manufacturing method of the detection substrate 1010 includes following steps.

Step 1: forming a first electrode 11 on a base substrate 10. For example, forming the first electrode 11 on the base substrate 10 can include forming a first electrode layer on the base substrate 10, and patterning the first electrode layer to form the first electrode 11. For further example, the method can include: depositing a conductive layer on the base substrate 10; spin coating a photoresist layer; and by using photolithography, exposing, developing to remove the exposed photoresist, etching the conductive layer which is not protected by the photoresist, and stripping off the remained photoresist to complete the manufacturing of the first electrode.

Figure 4A:
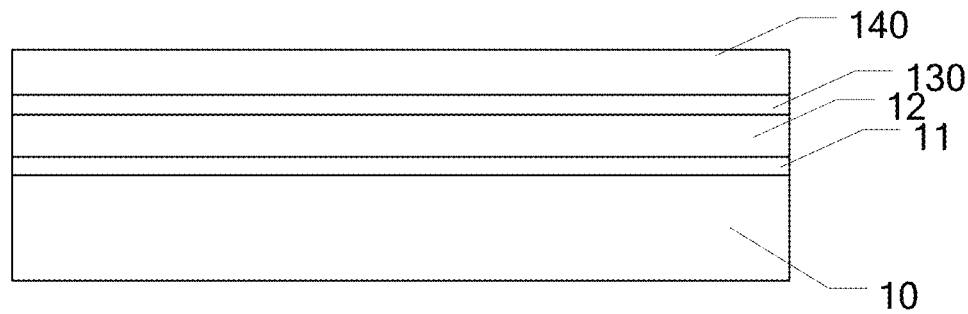
FIGS. 4a-4g are schematic diagrams of a manufacturing method of a detection substrate provided by an embodiment of the disclosure.

Step 2: as illustrated in FIG. 4a, forming a first passivation layer 12, a second electrode layer 130 and a photoresist layer 140 in sequence on the first electrode 11.

Figure 4B:
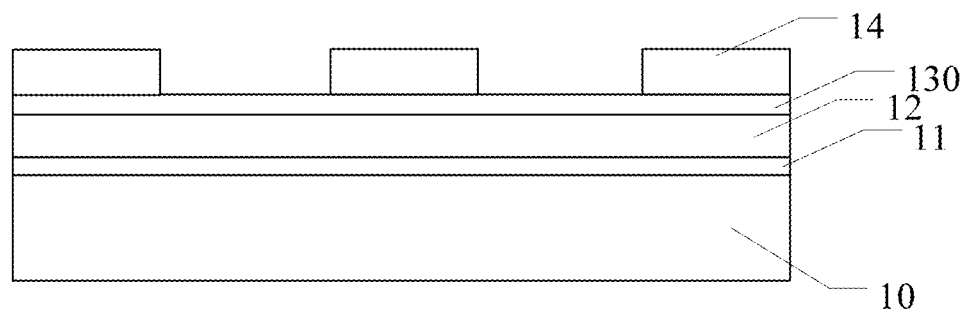

Step 3: as illustrated in FIG. 4b, exposing and developing the photoresist layer 140 to form a patterned photoresist 14.

Figure 4C:
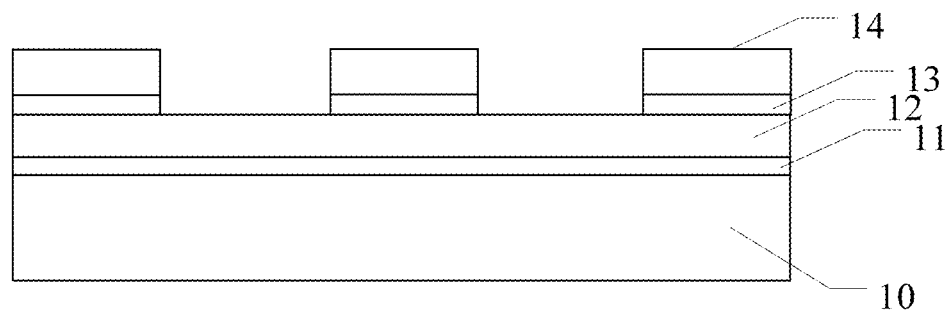

Step 4: as illustrated in FIG. 4c, etching the second electrode layer 130 by using the patterned photoresist 14 as a mask to obtain the second electrode 13. For example, the manufacturing method of the second electrode can be same as the manufacturing method of the first electrode, other than the patterns.

Figure 4D:
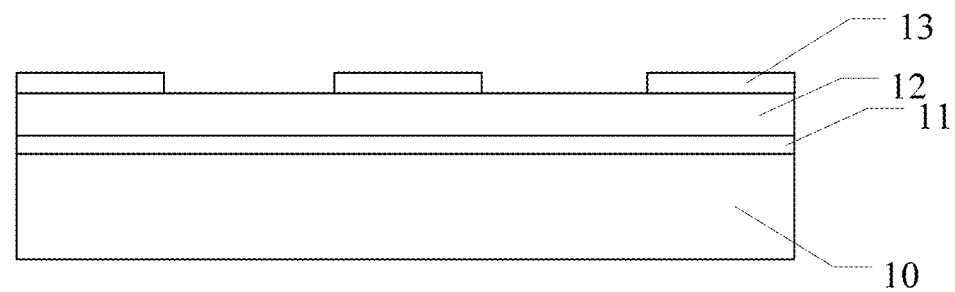

Step 5: as illustrated in FIG. 4d, stripping off the patterned photoresist 14.

Figure 4E:
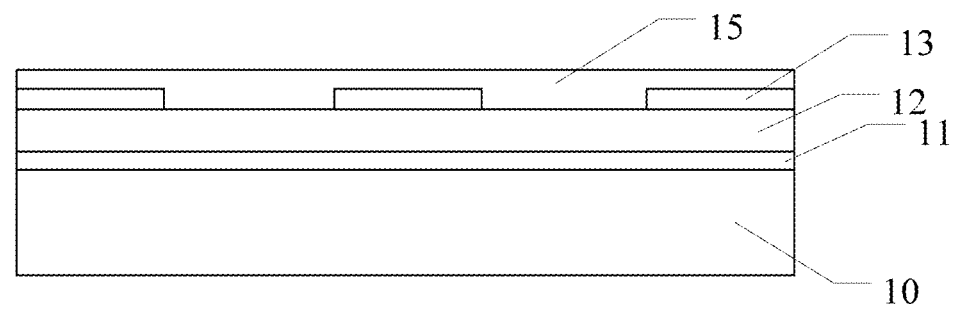

Step 6: as illustrated in FIG. 4e, forming a second passivation layer 15 on the second electrode 13.

Figure 4F:
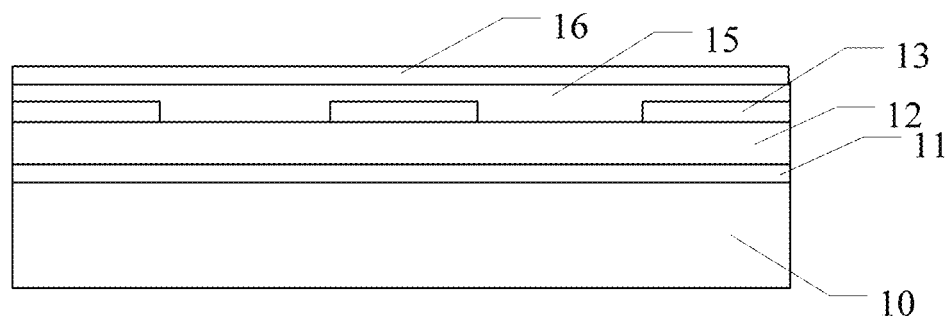

Step 7: as illustrated in FIG. 4f, forming a coupling layer 16 on the passivation layer 15.

Figure 4G:
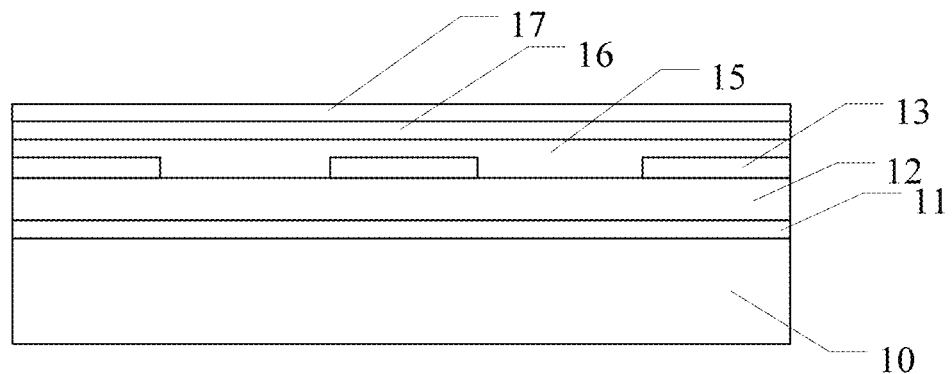

Step 8: as illustrated in FIG. 4g, forming a colloid layer 17 on the coupling layer 16, the colloid layer 17 including a linker 170 (not illustrated in FIG. 4g, please refer to FIG. 2a).

For example, a material of the first electrode 11 and/or the second electrode 13 can be a transparent conductive material. For example, the transparent conductive material can be conductive metal oxide, for further example, the conductive metal oxide includes indium tin oxide (ITO).

For example, the base substrate 10 can be Si or glass, etc., but it is not limited to this. For example, the detection substrate can be manufactured by a nano-imprinting technology.

The method of the embodiment can be adopted to manufacture any of the detection substrates 1010 of the first embodiment. Same or similar portions will not be repeated herein.

Third Embodiment

The embodiment provides a nucleic acid detecting method, including:

taking at least one detection unit 100 of any one of the detection substrates 1010 of the first embodiment as an active unit 0100, applying voltages with different polarities to the first electrode 11 and the second electrode 13 of the active unit respectively, a polarity of the voltage applied to the first electrode 11 of the active unit 0100 being opposite to a polarity of an electric charge of the target nucleic acid 18, and correspondingly, a polarity of the voltage applied to the second electrode 13 of the active unit 0100 being same as the polarity of the electric charge of the target nucleic acid 18;

flowing a library through the detection substrate 1010, a linker 170 in the active unit being paired with a target nucleic acid 18 of the library, and performing an amplification to form a target nucleic acid to be detected (a target nucleic acid cluster to be detected);

detecting the target nucleic acid to be detected. For example, the detecting process is a sequencing-by-synthesis process. For example, a sequence of the target nucleic acid can be obtained after detection.

For example, the target nucleic acid cluster to be detected includes a plurality of target nucleic acids to be detected.

At least one probe includes at least one nucleic acid that is complementary to at least a part of at least one target nucleic acid to be detected.

For example, at least one probe includes a plurality fluorescently labeled bases. For example, the at least one probe includes four fluorescently labeled deoxy-ribonucleoside triphosphates (dNTPs).

For example, the detection substrate 1010 includes a plurality of detection units 100, the first electrode 11 and the second electrode 12 of each of the detection units (inactive units) other than the active units are applied with voltages with same polarity. The polarity of the voltages with the same polarity is the same as the polarity of the electric charge of the target nucleic acid, so as to repel the target nucleic acid, and avoid the target nucleic from being paired with the linker within the inactive unit.

For example, the detection substrate includes a plurality of detection units 100. Different detection units are taken as the active unit in turn and voltages with same polarity are applied to the first electrode 11 and the second electrode 13 of each of the detection units 100 other than the active unit, different libraries are flowed through the detection substrate 1010 and the amplification and the detection are performed in different active units.

For example, detecting the target nucleic acid to be detected including:

contacting the detection substrate 1010 with at least one fluorescently labeled probe configured to be bound to the target nucleic acid to be detected;

detecting a fluorescent signal on the detection substrate 1010 to recognize the target nucleic acid to be detected bound with at least one probe.

Hereinafter, a description of a detecting method using a target DNA (template DNA or DNA template) as a target nucleic acid for gene sequencing will be given. An example in which the target nucleic acid 18 has a negative electric charge will be described.

Firstly, a positive voltage is applied to the first electrode 11 of the first detection unit 101, and a negative voltage is applied to the second electrode 13 of the first detection unit 101, both of the first electrode 11 and the second electrode 1 of other detection units are applied with a negative voltage, and then a first library is flowed through the detection substrate 1010, so that a target DNA of the first library is attracted to the first detection unit 101, and is paired with the liner 170 of the first detection unit 101.

Then, the first electrode 11 of the second detection unit 102 is applied with a positive voltage, and the second electrode 13 of the second detection unit 101 is applied with a negative voltage, both of the first electrode 11 and the second electrode 1 of other detection units are applied with a negative voltage, and then a second library is flowed through the detection substrate 1010, so that a target DNA of the second library is attracted to the second detection unit 102, and is paired with the liner 170 of the second detection unit 102.

Different detection units are taken as the active unit (in the active unit, the first electrode is positively charged and the second electrode is negatively charged) in turn, and then a corresponding library is flowed through the detection substrate 1010, so that respective libraries are separated from each other, and the polymerase chain reaction (PCR) is performed in different detection units to facilitate the amplification and the detection. There is no need to distinguish the libraries by using the barcode, thereby simplifying the sequencing flow, shortening the detection time and reducing the detection cost.

The first electrode and the second electrode of the detection unit are employed to perform the amplification and the detection of the target nucleic acid in the embodiments of the disclosure, the manufacturing process and the requirement on the structure and the appearance of the first electrode and the second electrode are simple, high throughput sequencing is achieved, and at the same time process difficulty is simplified, and there is no need to perform a surface polishing process, power-on condition of the first electrode and the second electrode of different detection units can be controlled, so as to control different libraries to be loaded to different regions, no barcode is needed to distinguish libraries and more libraries can be sequenced at one time, a precision control is achieved. Thus, a flow of the gene sequencing is simplified, a sequencing time is shortened and a sequencing cost is reduced For example, the library can be constructed by following process. A DNA sample to be detected is cut into small fragments by ultrasounds. Currently, except assembly and some other special requirements, the sample is principally cut into sequence fragments with a length of 200-500 bp (base pairs), and different linkers are added to two ends of each of the small fragments, to construct a single-stranded DNA library. For example, a linker in the target nucleic acid 18 can be configured to be paired with the linker 170.

For example, when the library is constructed, the DNA of these libraries will be attached to a surface of the active unit when these libraries are flowed through the detection substrate, and be paired with the linkers of the surface of the active unit. The surface of each of the detection units can be attached with a plurality of linkers, which can be paired with the linkers added to the two ends of the DNA during constructing the library, and can support that the bridge PCR amplification of the DNA is performed on the surface of the active unit.

For example, in the bridge PCR amplification and denaturation, the bridge amplification is performed through the bridge PCR by using the linker fixed on the surface of the detection unit as a template. After continuous amplification and denaturation cycles, finally, each of the DNA fragments will be clustered on respective positions, each of the clusters includes a lot of copies of a single target DNA (the target nucleic acid to be detected is formed). A purpose of this procedure is that signal strength of the base is enhanced, so as to reach a signal requirement for sequencing.

For example, in sequencing, the DNA polymerases, the linker primers and four fluorescently labeled deoxy-ribonucleoside triphosphates (dNTPs) are added to the reaction system at the same time. 3'-OH of these dNTPs are chemically protected, and thus only one dNTP is added at one time. After the dNTP is added to the synthetic strand, all of the unused free dNTP and DNA polymerase will be washed off. Next, a buffer solution for exciting fluorescence is added, a fluorescent signal is excited by laser, the fluorescent signal is recorded by an optical device, and finally, the optical signal is transformed to a sequencing base by computer analysis. After the record of the fluorescent signal is completed, the chemical reagent is added to quench the fluorescent signal and the protection group for protecting the 3'-OH of the dNTP is taken out, to perform a next cycle of the sequencing reaction.

For example, the term "library," when used in reference to analytes, refers to a collection of analytes having different chemical compositions. Typically, the analytes in a library will be different species having a common feature or characteristic of a genera or class, but otherwise differing in some way. For example, a library can include nucleic acid species that differ in nucleotide sequence, but that are similar with respect to having a sugar-phosphate backbone.

For example, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

The following statements should be noted:

(1) Unless otherwise defined, the same reference sign represents the same meaning in the embodiments of the disclosure and accompanying drawings.

(2) The accompanying drawings involve only the structure(s) in connection with the embodiment(s) of the present disclosure, and other structure(s) can be referred to common design(s).

(3) For the purpose of clarity only, in accompanying drawings for illustrating the embodiment(s) of the present disclosure, the thickness and size of a layer or a structure may be enlarged. However, it should understood that, in the case in which a component or element such as a layer, film, area, substrate or the like is referred to be "on" or "under" another component or element, it may be directly on or under the another component or element or a component or element is interposed therebetween.

(4) In case of no conflict, features in one embodiment or in different embodiments can be combined.

What are described above is the embodiments of the disclosure only and not limitative to the scope of the disclosure; any of those skilled in related arts can easily conceive variations and substitutions in the technical scopes disclosed by the disclosure, which should be encompassed in protection scopes of the disclosure. Therefore, the scopes of the disclosure should be defined in the appended claims.

The invention claimed is:

1. A detection substrate comprising at least one detection unit disposed on a base substrate, the at least one detection unit comprising:

a first electrode;

a first passivation layer, located on the first electrode;

a second electrode, located on the first passivation layer, the second electrode comprising a plurality of sub-electrodes arranged in an array, the second electrode and the first electrode being insulated from each other, and the first electrode and the second electrode being configured to be applied with voltages, respectively;

a second passivation layer, located on the second electrode, the second passivation layer covering and filling in between the sub-electrodes arranged in the array; and a colloid layer, located on the second passivation layer and at least disposed in a region corresponding to a region enclosed by adjacent sub-electrodes of the plurality of sub-electrodes, the colloid layer comprising a linker configured to be paired with a target nucleic acid, wherein the first electrode is configured to be applied with a voltage having a polarity opposite to a polarity of an electric charge of the target nucleic acid, and the second electrode is configured to be applied with a voltage having a polarity the same as the polarity of the electric charge of the target nucleic acid.

2. The detection substrate according to claim 1, wherein the first electrode and the second electrode are configured to be applied with voltages with different polarities, respectively.

3. The detection substrate according to claim 1, wherein in a direction perpendicular to the base substrate, the first electrode is overlapped with the region enclosed by the adjacent sub-electrodes of the plurality of sub-electrodes and is overlapped with the plurality of sub-electrodes.

4. The detection substrate according to claim 1, wherein the first electrode is a plane-shaped electrode.

5. The detection substrate according to claim 1, wherein the plurality of sub-electrodes are electrically connected.

6. The detection substrate according to claim 1, wherein the region enclosed by the adjacent sub-electrodes of the plurality of sub-electrodes is filled by a part of the second passivation layer.

7. The detection substrate according to claim 1, further comprising a coupling layer disposed between the second passivation layer and the colloid layer.

8. The detection substrate according to claim 7, wherein a material of the coupling layer comprises silane.

9. The detection substrate according to claim 1, wherein the colloid layer comprises a gel layer.

10. A nucleic acid detecting method using a detection substrate,
the detection substrate comprising at least one detection unit disposed on a base substrate, the at least one detection unit comprising:
a first electrode;
a first passivation layer, located on the first electrode;
a second electrode, located on the first passivation layer, the second electrode comprising a plurality of sub-electrodes arranged in an array, the second electrode and the first electrode being insulated from each other, and the first electrode and the second electrode being configured to be applied with voltages, respectively;
a second passivation layer, located on the second electrode, the second passivation layer covering and filling in between the sub-electrodes arranged in the array; and
a colloid layer, located on the second passivation layer and at least disposed in a region corresponding to a region enclosed by adjacent sub-electrodes, the colloid layer comprising a linker configured to be paired with a target nucleic acid,
wherein the first electrode is configured to be applied with a voltage having a polarity opposite to a polarity of an electric charge of the target nucleic acid, and the second electrode is configured to be applied with a voltage having a polarity the same as the polarity of the electric charge of the target nucleic acid,
the nucleic acid detecting method comprising:
taking the at least one detection unit as an active unit, applying voltages with different polarities to the first electrode and the second electrode of the active unit, respectively, the voltage applied to the first electrode of the active unit having a polarity opposite to the polarity of the electric charge of the target nucleic acid;
flowing a library through the detection substrate, the linker in the active unit being paired with a target nucleic acid of the library, and performing an amplification to form a target nucleic acid to be detected; and
detecting the target nucleic acid to be detected.

11. The nucleic acid detecting method according to claim 10, wherein a first electrode and a second electrode of detection units other than the active unit are applied with voltages with a same polarity, the polarity of the voltages applied to the first electrode and the second electrode of the detection units other than the active unit is the same as the polarity of the electric charge of the target nucleic acid.

12. The nucleic acid detecting method according to claim 10, wherein different detection units are taken as the active unit sequentially, and a first electrode and a second electrode of detection units other than the active unit are applied with voltages having a same polarity as that of the electric charge of the target nucleic acid, different libraries are flowed through the detection substrate to perform the amplification and the detection in different active units.

13. The nucleic acid detecting method according to claim 10, wherein detecting the target nucleic acid to be detected comprises:
contacting the detection substrate with at least one fluorescently labeled probe configured to be bound to the target nucleic acid to be detected; and
detecting a fluorescent signal on the detection substrate to recognize the target nucleic acid to be detected bound with the at least one probe.

14. The detection substrate according to claim 1, wherein two adjacent ones of the plurality of sub-electrodes are connected by a connecting sub-electrode to form an annular electrode pattern, a width of the connecting sub-electrode is less than that of each of the plurality of sub-electrodes.

15. The detection substrate according to claim 1, wherein a plurality of detection units are provided, first electrodes of different detection units are separated from each other, and second electrodes of different detection units are separated from each other.

16. The detection substrate according to claim 15, wherein a gap region is provided between the different detection units, and a part of the colloid layer located in the gap region is inactive.

17. The detection substrate according to claim 5, wherein the plurality of sub-electrodes are electrically connected by a plurality of connecting sub-electrodes, every four adjacent sub-electrodes in the plurality of sub-electrodes are electrically connected by four of the plurality of connecting sub-electrodes.

18. The detection substrate according to claim 1, wherein first electrodes of different detection units are separated from each other, and second electrodes of the different detection units are separated from each other.

* * * * *